United States Patent [19]

Soloviev et al.

[11] 4,417,579

[45] Nov. 29, 1983

[54] DEVICE FOR MARKING OUT THE CORNEA IN OPHTHALMOSURGICAL OPERATIONS

[75] Inventors: Sergei A. Soloviev; Svyatoslav N. Fedorov; Vitaly P. Osetsky, all of Moscow, U.S.S.R.; Valery V. Durnev, deceased, late of Moscow, U.S.S.R., by Tamara S. Durneva, administratrix

[73] Assignee: Moskovsky Nauchno-Issledovatelsky Institut Mikrokhirurgii Glaza, Moscow, U.S.S.R.

[21] Appl. No.: 373,492

[22] PCT Filed: Aug. 22, 1980

[86] PCT No.: PCT/SU80/00140

§ 371 Date: Apr. 16, 1982

§ 102(e) Date: Apr. 16, 1982

[87] PCT Pub. No.: WO82/00584

PCT Pub. Date: Mar. 4, 1982

[51] Int. Cl.³ .............................................. A61F 9/00
[52] U.S. Cl. .................................. 128/303 R; 128/305; 33/191
[58] Field of Search ............ 128/303 R, 305; 33/189, 33/191

[56] References Cited

U.S. PATENT DOCUMENTS 3,502,070  3/1970  Bliss ................................. 128/303 R
4,205,682  6/1980  Crock et al. ....................... 128/305

OTHER PUBLICATIONS

A. Toufexis "Shaping up the Blurry Eye" *Time* Sep. 22, 1980 p. 51.

*Primary Examiner*—William E. Kamm
*Assistant Examiner*—Mitchell J. Shein
*Attorney, Agent, or Firm*—McAulay, Fields, Fisher, Goldstein & Nissen

[57] ABSTRACT

According to the present invention, the device comprises a body 1 in the form of a bush with a central hole 2 accommodating a sighting aligning device 3, and a number of plates at one of the bush ends, arranged in the planes square with the plane of the sighting device and adapted to get in contact with the cornea being marked out. The face edges 9 of the plates 8 are made curved and their thickness is so selected that upon applying a required force thereto the edges would cause elastic non-destructive deformation of the cornea. The mutual arrangement of the plates depends upon the required arrangement of incisions during operation.

6 Claims, 5 Drawing Figures

DEVICE FOR MARKING OUT THE CORNEA IN OPHTHALMOSURGICAL OPERATIONS

FIELD OF THE INVENTION

The present invention relates generally to ophthalmology and has particular reference to a device for marking out the cornea in ophthalmosurgery; the invention can find successful application in operation for elimination of astigmatism, myopia, or complex myopic astigmatism.

BACKGROUND OF THE INVENTION

A novel surgical method of treating such eye diseases as astigmatism myopia and complex myopic astigmatism has attracted much attention within the recent years. When carrying out this method the ophthalmosurgeon makes a number of non-perforating incisions in the cornea. Depending on the particular eye disease and the conditions of the patient's eye being treated, an appropriate arrangement of incisions is to be selected. In the present-day practice the surgeon has to find the required arrangement of incisions approximately and then makes the incisions.

Admittedly, the abovesaid method of making incisions in the cornea fails to provide pin-point accuracy of their arrangement both with respect to one another and relative to the optical centre of the eye and the patient's facial axis of symmetry. However, but a small inaccuracy in making incisions might lead to objectionable results for the patient operated upon, viz., distortion of the optical pathway of the light rays in the eye, which results in distorted image perceptible by the eye.

DISCLOSURE OF THE INVENTION

It is therefore a primary and essential object of the present invention to provide such a device for marking out the cornea in ophthalmosurgery that would enable the surgeon to make incisions in the cornea at a precision accuracy to suit the particular disease, thus attaining reliable results in ophthalmosurgical operations.

The aforesaid object is accomplished due to the fact that a device for marking out the cornea in ophthalmosurgery, according to the present invention, comprises a body in the form of a bush having a central hole, which accommodates a sighting aligning device, and plates provided at one of the bush ends in the planes square with the plane of the sighting device and adapted to get in contact with the cornea being marked out, while the face edges of the plates are curved and their thickness is so selected that, upon applying a preset force thereto, said edges would cause elastic non-destructive deformation of the cornea, whereas the mutual arrangement of the plates depends upon the required arrangement of incisions made during operation.

The herein-proposed invention is based upon the fact established by the inventors that plastic behaviour of the cornea makes it possible to obtain imprinted marks thereon that would persist for a lapse of time long enough to make incisions in the cornea. The present invention is advantageous in that it provides for an accurate arrangement of incisions so as to suit the nature of the eye disease the patient suffers from and hence the operation involved. With a set of such devices at hand the surgeon is in a position of selecting a required device, wherein the plates are arranged in a pattern necessary for performing a given operation.

In one of the embodiments of the device adapted for surgical treatment of myopia the plates are spaced apart at a constant angular pitch along the circumference of the bush end and, to provide an adequate illumination in the case where the plates are held to the bush end flange, a number of through holes are made in the flange from inside.

For other types of surgical interventions the plates are arranged in groups, the mutual arrangement of the plates in the group and that of the groups of plates being dependent upon the nature of the operation performed.

It is expedient to provide a drum inside the bush coaxially therewith, said drum being mounted with a possibility of being swivelled and locked in a required position and having a through hole accommodating a sighting device, as well as a means to read the drum angular position.

Such a constructional arrangement provides for correct orienting of the entire device with respect to the optical centre of the eye and the facial axis of symmetry.

Furthermore, the sighting device is expedient to be traversable along the bush longitudinal axis in order to change its position with respect to the edges of the plates to suit a change in focussing the optical system.

BRIEF DESCRIPTION OF THE ACCOMPANYING DRAWINGS

In what follows the present invention is illustrated by a detailed description of specific embodiments of a device for marking out the cornea, according to the present invention, to be read in conjunction with the accompanying drawings, wherein.

BEST MODE OF CARRYING THE INVENTION INTO EFFECT

Figure 1:
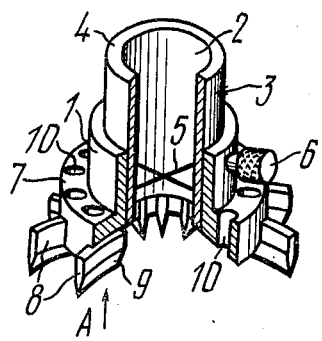
FIG. 1 is a perspective fragmentarily cutaway view of a device for marking out the cornea in ophthalmosurgery.

Referring now to the accompanying drawings FIG. 1 represents a device for marking out the cornea, comprising a body 1 made as a bush with a central through hole 2, which accommodates a sighting device 3 made as a ring 4 to which cross-hairs 5 are fixed rigidly. The cross-hairs are expedient to be arranged along the axis of the central hole 2.

The ring 4 can be rigidly fixed axially with the help of a screw 6.

An end flange 7 is provided at the bottom end of the bush to hold plates 8 arranged in the planes square with the plane of the sighting device, more specifically, in the plane passing through the cross-hairs 5. Each of the plates 8 is made from a material capable of providing the best sterile conditions, e.g., from a stainless alloy, or from a material provided with anticorrosion coating. A bottom face edge 9 of the plates 8 is made curved, and the radius of its curvature is preferable to correspond to the radius of curvature of the patient's cornea, while the thickness of the edges 9 is so selected as to provide elastic non-destructive deformation of the cornea. As a rule, the thickness of the edges of the plate 8 is selected to be within 0.1 and 0.2 mm.

In addition, a number of through holes 10 are provided in the inner surface of the flange 7 for better illumination of the sighting device 3.

FIG. 1 illustrates the plates spaced apart at a constant angular pitch along the circumference of the bush end, such an arrangement being used for marking out the cornea in myopia correction operations. Some other versions of the mutual arrangement of the plates are also practicable as hereinafter shown in detail. At any rate the mutual arrangement of the plates depends upon the operation being performed. The manipulation with the afore-described device by surgeon is as follows.

Having knowledge of the size of the patient's central optical zone the surgeon selects such a device for marking out the cornea that features the edges of the plates facing the central hole 2 lying on a curve corresponding to the margin of the optical zone of the patient's cornea. Having selected a required device and adjusted the axial position of the sighting device 3 to suit the optical system (microscope) used in the course of operation, the surgeon locks the sighting device in that position against axial displacement by a screw 6.

Figure 5:
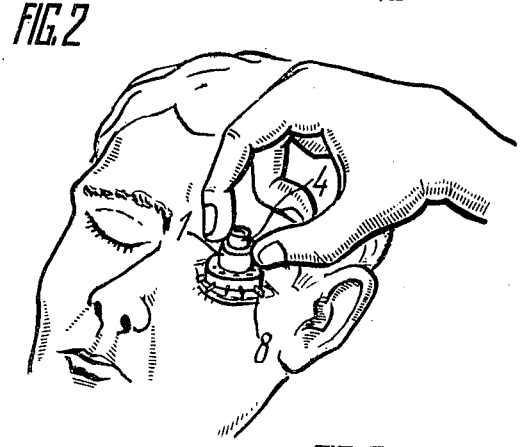
FIG. 5 illustrates a mutual arrangement of the patient's eye and the device in the course of operation.

Then the surgeon proceeds to marking out. To this effect the surgeon brings the cross-hairs 5 of the sighting device 3 in register with the optical centre of the patient's cornea and presses the device for 2 or 3 seconds with the face edges 9 of the plates 8 against the patient's cornea as shown in FIG. 5.

Once the device has been removed from the cornea well perceptible imprinted marks are left on the latter against which the surgeon can perform incisions.

Figure 2:
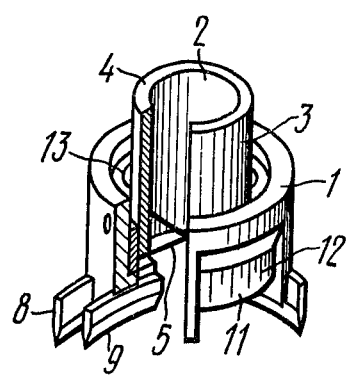
FIG. 2 is a device for marking out the cornea in ophthalmosurgery substantially similar to the device of FIG. 1 but having a drum and featuring another mutual arrangement of the plates.

The device shown in FIG. 2 is chiefly identical to that described with reference to FIG. 1 and similar components therein are indicated at the same Reference Numerals, the only difference being a drum 11 provided with a possibility of being swivelled round the axis of the device and having a means for reading its angular position with respect to the body 1, said means being essentially graduation marks 12. The drum is kept against accidental rotation round the axis of the device by a coil spring 13 fixed in place on the body 1 so as to force the end face of the drum 11.

Figure 3:
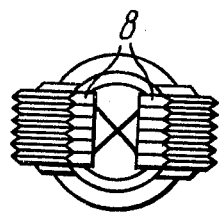
FIG. 3 is a bottom view along the arrow A in FIG. 1 to indicate a possible embodiment of the mutual arrangement of the plates.

The abovesaid construction of the device makes provision for the arrangement of the plates 8 as shown in FIG. 3 as intended for astigmatism correction operations, i.e., there are two groups of the plates 8 situated on the diametrically opposite sides of the body, while the plates in each of the groups are arranged parallel to one another.

Figure 4:
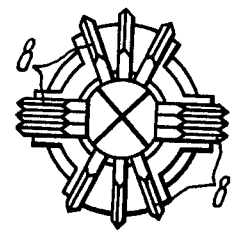
FIG. 4 shows one more possible embodiment of the mutual arrangement of the plates.

Some other kinds of mutual arrangement of the plates in groups and of the groups may be used for treating other types of complex astigmatism, e.g., myopic astigmatism, as shown in FIG. 4, wherein two groups of parallel plates are arranged diametrically opposite, whereas two groups of plates are spaced apart at a constant angular pitch.

Operation with the device as shown in FIG. 2 is carried out substantially as with that described with reference to FIG. 1, the only difference residing in that prior to marking out the cornea the surgeon sets the drum 11 with the sighting device 3 to a certain position preset for a given operation, with respect to the body 1 of the device against the graduation marks 12 and, while marking out the cornea, the surgeon must keep one of the hairs of the cross-hairs 5 parallel with the facial axis of symmetry depending upon the readings taken on the graduation marks.

INDUSTRIAL APPLICABILITY

The device of the present invention aimed at marking out the cornea in ophthalmosurgery can find successful application in elimination of astigmatism, myopia, or complex myopic astigmatism; it enables one to prevent the onset of postoperative astigmatism and cut down the operating time 2 or 3 times.

We claim:

1. Means for marking out the cornea in ophthalmosurgical operations, characterized in that said means contains a body 1 in the form of a bush having a central hole 2, said central hole accomodating a sighting aligning device 3, and plate means 8 provided at one of the bush ends in the planes square with the plane of said sighting device 3 and further said plate means adapted to contour to the cornea being marked out, while the face edges 9 of the plates 8 are curved and their thickness is so selected that, upon applying a preset force thereto, said edges would cause elastic non-destructive deformation of the cornea, whereas the mutual arrangement of the plates depends upon the required arrangement of incisions made during operation.

2. Means as claimed in claim 1, characterized in that the plates 8 are spaced apart at a constant angular pitch along the circumference of the bush end.

3. Means for marking out the cornea as claimed in claim 2, characterized in that the bush has an end flange 7 to which the plates are held, said flange having a number of through holes 10 provided in its inner surface.

4. Means as claimed in claim 1, characterized in that the plates are arranged in groups.

5. Means as claimed in claim 4, characterized in that a drum 1 having a through axial hole is provided inside the bush coaxially therewith capable of being swivelled and held in a required position, said drum 11 including means 12 for reading its angular position and carrying a sighting device accommodated inside its axial hole.

6. Means as claimed in claims 1, 2, 3, 4, or 5, characterized in that the sighting device is traversable along the bush longitudinal axis so as to change its position with respect to the edges of said plate means to suit a change in focussing the optical system.

* * * * *